(12) United States Patent
Morrison et al.

(10) Patent No.: US 9,737,333 B2
(45) Date of Patent: Aug. 22, 2017

(54) STEERABLE MEDICAL PUNCTURE INSTRUMENT

(71) Applicant: AprioMed AB, Uppsala (SE)

(72) Inventors: William B. Morrison, Philadelphia, PA (US); Dan Akerfeldt, Uppsala (SE)

(73) Assignee: Apriomed AB, Uppsala (SE)

( * ) Notice: Subject to any disclaimer, the term of this patent is extended or adjusted under 35 U.S.C. 154(b) by 44 days.

(21) Appl. No.: 14/326,052

(22) Filed: Jul. 8, 2014

(65) Prior Publication Data

US 2014/0379017 A1 Dec. 25, 2014

Related U.S. Application Data

(63) Continuation of application No. 13/146,589, filed as application No. PCT/US2009/064549 on Nov. 16, 2009.

(60) Provisional application No. 61/147,844, filed on Jan. 28, 2009, provisional application No. 61/187,057, filed on Jun. 15, 2009.

(51) Int. Cl.
*A61B 17/34* (2006.01)
*A61B 17/00* (2006.01)

(52) U.S. Cl.
CPC .... *A61B 17/3417* (2013.01); *A61B 2017/003* (2013.01)

(58) Field of Classification Search
CPC  A61B 2017/22072; A61B 2017/22074; A61B 2017/003; A61B 2017/00309; A61B 2017/00318; A61B 2017/00314; A61B 2017/00323; A61B 17/3417; A61B 17/34; A61B 17/3401; A61B 17/3421; A61B 17/3431; A61B 17/3478; A61B 10/0233; A61B 2010/045

See application file for complete search history.

(56) References Cited

U.S. PATENT DOCUMENTS

| | | | |
|---|---|---|---|
| 4,529,400 A | * | 7/1985 | Scholten ........... A61M 25/0138 128/207.14 |
| 4,815,478 A | | 3/1989 | Buchbinder et al. |
| 4,874,376 A | | 10/1989 | Hawkins, Jr. |
| 4,886,067 A | | 12/1989 | Palermo |
| 5,662,119 A | | 9/1997 | Brennen et al. |

(Continued)

FOREIGN PATENT DOCUMENTS

| | | |
|---|---|---|
| WO | 2005105191 A2 | 11/2005 |
| WO | 2008001385 A2 | 1/2008 |

*Primary Examiner* — Julie A Szpira
(74) *Attorney, Agent, or Firm* — Pierce Atwood LLP; Kevin M. Farrell; David J. Wilson

(57) ABSTRACT

The invention is directed to a steerable mandrel comprising a stationary part and a movable part. The stationary part comprises a tubular sleeve having a mantle wall with a longitudinal semi-circumferential opening or weakening, which divides the stationary part into a proximal portion located on a proximal side of the longitudinal semi-circumferential opening or weakening and a distal portion located on distal side of the longitudinal semi-circumferential opening or weakening. The movable part comprises a rod-like member, which is slidable within the proximal portion of the stationary part. The movable part is attached to distal portion of the stationary part, such that relative movement of the movable part in relation to the stationary part causes a bending of the mandrel.

4 Claims, 5 Drawing Sheets

(56) References Cited

U.S. PATENT DOCUMENTS

| | | | |
|---|---|---|---|
| 6,132,390 A | 10/2000 | Cookston et al. | |
| 6,206,870 B1* | 3/2001 | Kanner | A61B 17/2909 604/523 |
| 6,248,112 B1 | 6/2001 | Gambale et al. | |
| 6,319,195 B1* | 11/2001 | Nakaichi | A61B 1/0052 600/120 |
| 6,419,641 B1 | 7/2002 | Mark et al. | |
| 6,623,448 B2 | 9/2003 | Slater | |
| 6,652,491 B1 | 11/2003 | Walker et al. | |
| 7,056,314 B1 | 6/2006 | Florio et al. | |
| 7,077,823 B2 | 7/2006 | McDaniel | |
| 7,101,361 B2 | 9/2006 | Gardeski | |
| 7,449,002 B1 | 11/2008 | Wenstad | |
| 8,641,697 B2 | 2/2014 | Partlett et al. | |
| 8,677,990 B2* | 3/2014 | Gabriel | A61B 1/2673 128/200.26 |
| 2003/0130712 A1 | 7/2003 | Smits et al. | |
| 2004/0133168 A1 | 7/2004 | Salcudean et al. | |
| 2007/0021767 A1* | 1/2007 | Breznock | A61B 17/00234 606/185 |
| 2008/0097347 A1 | 4/2008 | Arvanaghi | |
| 2008/0161809 A1 | 7/2008 | Schmitz et al. | |

* cited by examiner

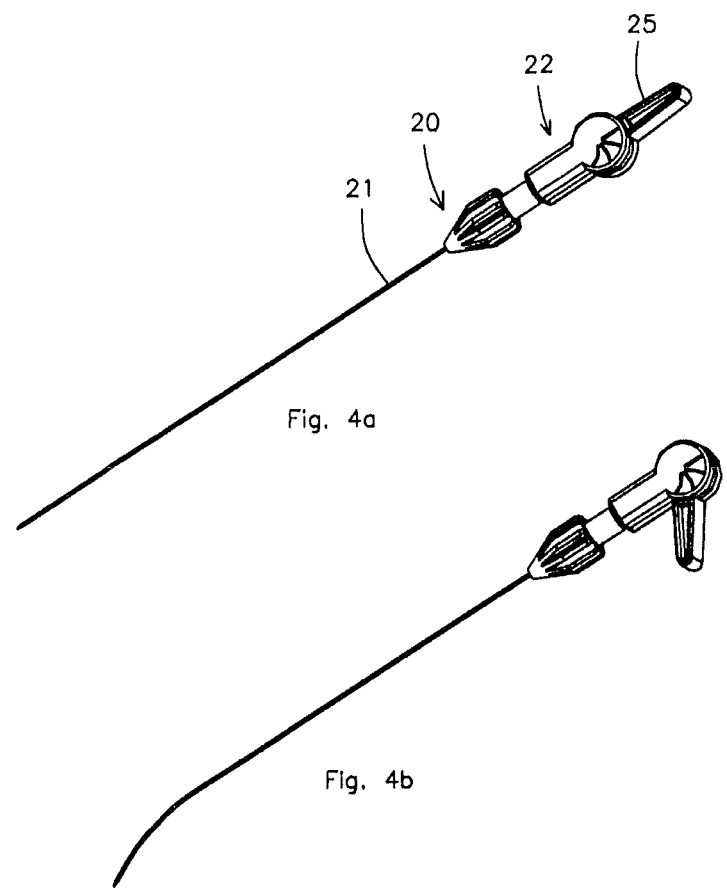
Fig. 4a
Fig. 4b
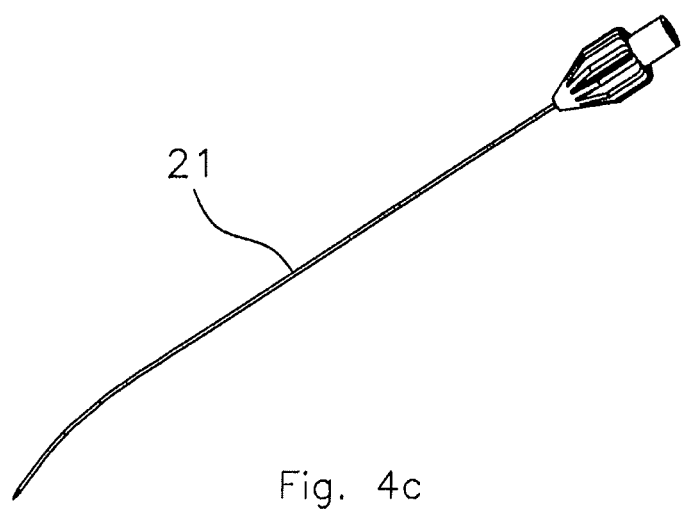
Fig. 4c

STEERABLE MEDICAL PUNCTURE INSTRUMENT

FIELD OF THE INVENTION

The present invention relates generally to medical puncture instruments used for penetration of tissues in human or animal beings, and more specifically to a steerable needle, also referred to as a mandrel or stylet, used for the guiding of a penetrating medical instrument.

BACKGROUND OF THE INVENTION

A problem with minimally invasive, percutaneous procedures is the limited control the operator has over the penetrating instrument once the instrument in question has been introduced beneath the skin of a patient; that is, the operator has only direct control over the insertion depth.

To achieve a higher degree of control, steerable devices, like needles and stylets, have been suggested. The U.S. Patent Application No. 2004/0133168 discloses a needle guidance system comprising a stylet with a curved tip portion. The radius of curvature is, however, fixed, such that a specific curvature and a specific length of the curved portion have to be selected for the specific application at hand.

U.S. Pat. No. 6,652,491 is related to a stylet made from a shape-memory material. To introduce a curvature in the stylet, the stylet has to be heated.

A general object of the present invention is to provide an improved design for a steerable penetrating medical instrument, which enhances the manoeuvrability and thereby the control of the penetrating instrument.

SUMMARY OF THE INVENTION

The above-mentioned object is achieved by the present invention according to the independent claims.

Preferred embodiments are set forth in the dependent claims.

Embodiments of the present invention are directed to a steerable mandrel, also referred to as a needle or stylet, which comprises a stationary part and a movable part. The movable part is attached to a distal portion of the stationary part in such a way that longitudinal movement of the movable part induces a bending of the stationary part and thereby a bending of the mandrel, at a distal portion thereof. By this arrangement, a steerable mandrel is provided, which is easy and safe to manoeuvre and whose bendable distal portion exhibits a radius of curvature that continuously can assume any curvature from no bending to a maximum curvature.

BRIEF DESCRIPTION OF THE DRAWINGS

FIG. 4a-c illustrate another medical instrument comprising the mandrel of FIG. 1 and a sleeve as well as handle for operating and steer the medical instrument.

DETAILED DESCRIPTION OF PREFERRED EMBODIMENTS

Figure 1:
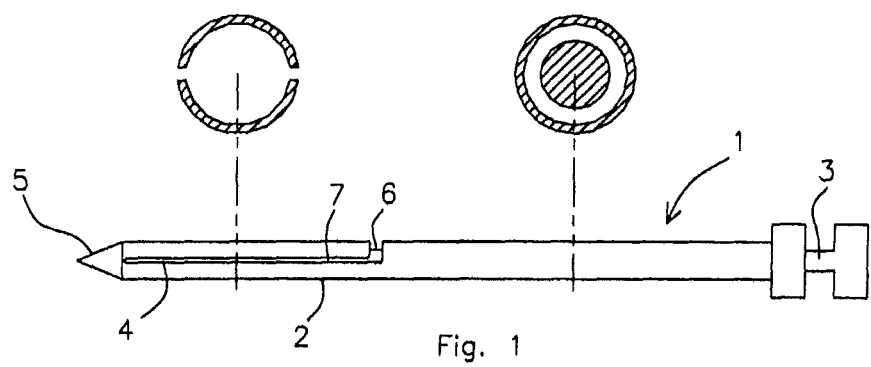
FIG. 1 shows a longitudinal cross-section of a first embodiment of a steerable mandrel according to the present invention.

FIG. 1 shows a longitudinal cross-section of a steerable mandrel 1 according to the present invention. The mandrel 1, which also can be referred to as a stylet or needle, comprises two parts: a stationary part 2 and a movable part 3. The stationary part 2 comprises basically a hollow tube or sleeve, with a mantle wall, in which two slits 4 have been provided at a distal portion thereof. The slits 4 extend longitudinally on opposite sides in the mantle wall at the distal portion of the stationary part 2. The slits 4 do not extend all the way to the distal end of the stationary part 2, but end a distance proximally of the distal end of the stationary part, such that a non-slit end 5 is provided. The distal end 5 can be blunt or sharp, where the latter option is shown in the drawings. At the proximal side of slits 4, a small, semi-circular portion of the mantle wall has been cut away, such that the slits 4 end a short distance before the mantle of the hollow tube or sleeve commences at the proximal portion of the stationary part 2. In this way, the stationary part 2 is provided with a transverse gap or notch 6 at the proximal end of the slits 4.

The movable part 3 comprises basically a piston-like elongated member 3, which is slidable within the hollow stationary part 2. More specifically, the movable part 3 comprises a distal end 7, which is attached to the distal portion of the stationary part; and more specifically, the distal end 7 of the movable part 3 extends beneath the notch 6 and is attached to the mantle wall of the stationary part in close proximity to the distal side of the notch 6. Preferably, the distal end 7 of the movable part 3 is attached to the distal portion of the stationary part 2 at the same circumferential position as the notch 6 is provided in the mantle wall thereof (as is indicated in FIG. 1).

Figure 2A:
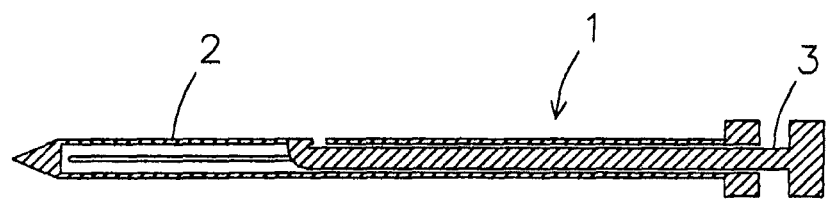
FIGS. 2a-c illustrate schematically the functioning of the steerable mandrel shown in FIG. 1.
Figure 2B:
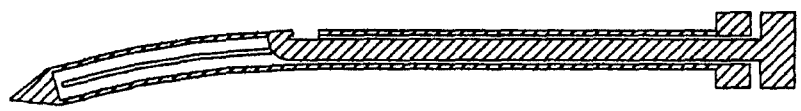
Figure 2C:
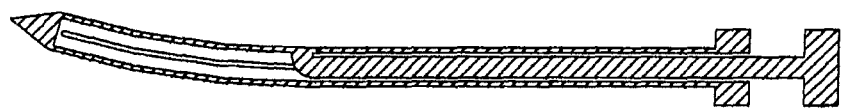

In FIGS. 2a, 2b and 2c the functioning of the steerable mandrel 1 is illustrated schematically. In FIG. 2a the stationary part 2, and in particular the distal portion thereof, and the movable part 3 are aligned with each other in a first or neutral position. In FIG. 2b, the movable part 3 has been pushed into the stationary part 2. Due to the attachment of the distal end of the movable part 3 at the distal side of the notch 6, this movement causes a widening of the notch 6, which in turn induces a bending of the distal portion of the stationary part 2. In FIG. 2b this bending is illustrated as bending in the downward direction. FIG. 2c illustrates a bending in the upward direction, where the movable part 3 has been retracted a short distance out of the stationary part 2. This movement causes a narrowing of the notch 6, which in turn leads to a bending of the distal portion of the stationary part 2 in a direction which is opposite to the direction caused by the pushing action described in conjunction with FIG. 2b.

Figure 3A:
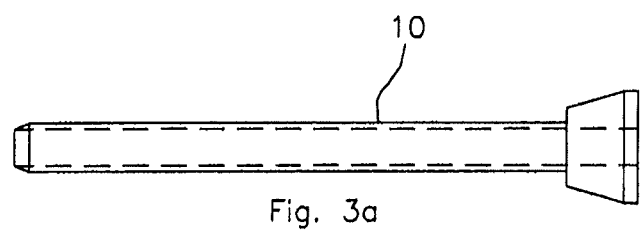
FIGS. 3a-c show how the mandrel of FIG. 1 can be combined with a sleeve to form a steerable and penetrating medical instrument.
Figure 3B:
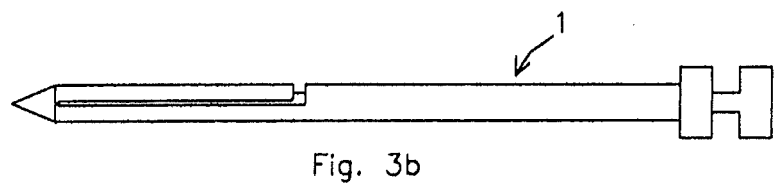
Figure 3C:
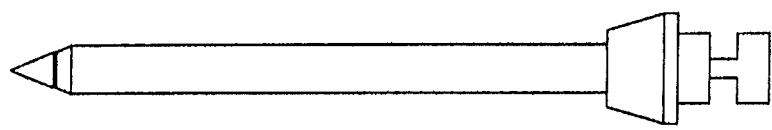

The mandrel 1 alone can be used as a medical tool. If the mandrel 1 is provided with a sharp distal end, the mandrel 1 can be regarded as a steerable needle 1. It is, however, within the scope of the present invention that the mandrel 1 is part of a medical tool, which, besides the mandrel 1, also comprises a sleeve 10. The sleeve 10 and the mandrel 1 are separately depicted in FIGS. 3a and 3b, respectively; and are depicted in an assembled state in FIG. 3c. The sleeve 10 should be made from elastic, i.e. bendable, material, such as a thin tube made from steel, preferably stainless steel, or nitinol. Preferably, also the mandrel 1 is made from steel or nitinol.

In use, the sleeve 10, with the mandrel or needle 1 inserted therein, is pushed through the skin of a patient, and is steered through tissue located beneath the skin to the target site of interest. By moving the movable part 3 relative to the stationary part 2, a bending of the mandrel or needle 1 is effectuated and thereby a corresponding bending of the sleeve 10. In this way the sleeve 10 can be steered in a desired way through the patient's body. A steering capability is, for example, desired when a target site is not located in a straight line from a desired entry point at the skin of patient. When the target site has been reached, the mandrel 1 can be removed, leaving only the sleeve 10 in place. Access to a desired location within a patient's body has thereby been obtained; presumably while sensitive or impenetrable areas located between the target site and the skin have been circumvented.

A somewhat more elaborated tool according to the present invention is illustrated in FIGS. 4a to 4b. FIG. 4a shows a medical instrument 20 in a first, neutral position. The medical instrument 20 comprises a sleeve 21, which is separately illustrated in FIG. 4c, and a mandrel 22. The mandrel 22 comprises, like mandrel 1, a stationary part and a movable part. In this embodiment, the movable part is, at its proximal end, provided with a handle 25, which is attached to an elongated, piston-like member, like in the embodiment shown in FIG. 1. By turning handle 25 in a first direction, the movable part is moved relative to the stationary part, such that the distal portion of the stationary part is bent in a first direction; and by turning handle 25 in a second and opposite direction, the distal portion of the stationary part is bent in a second and opposite direction. By providing a turnable handle 25, the mandrel 22 and the sleeve 21 are locked in a desired bending. When the target site of interest has been reached, the mandrel 22 can be removed, leaving only the sleeve 21 in place.

It should be appreciated that the slits 4 and notch 6 can have a wide variety of geometries and also need not pass completely through the mantle wall (they can comprise a weakened area of the mantle wall). As another example, other ways of exerting force, offset from the centreline of the stationary part, on the distal end of the stationary part may be used.

Figure 5B:
FIGS. 5a-e show cross-sections of a second embodiment of a steerable mandrel according to the present invention.
Figure 5A:
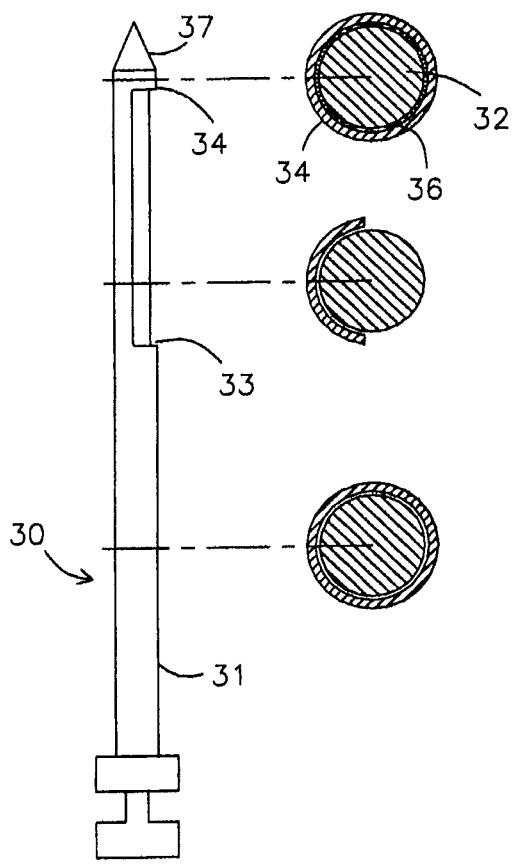
Figures 5C, 5D, 5E:
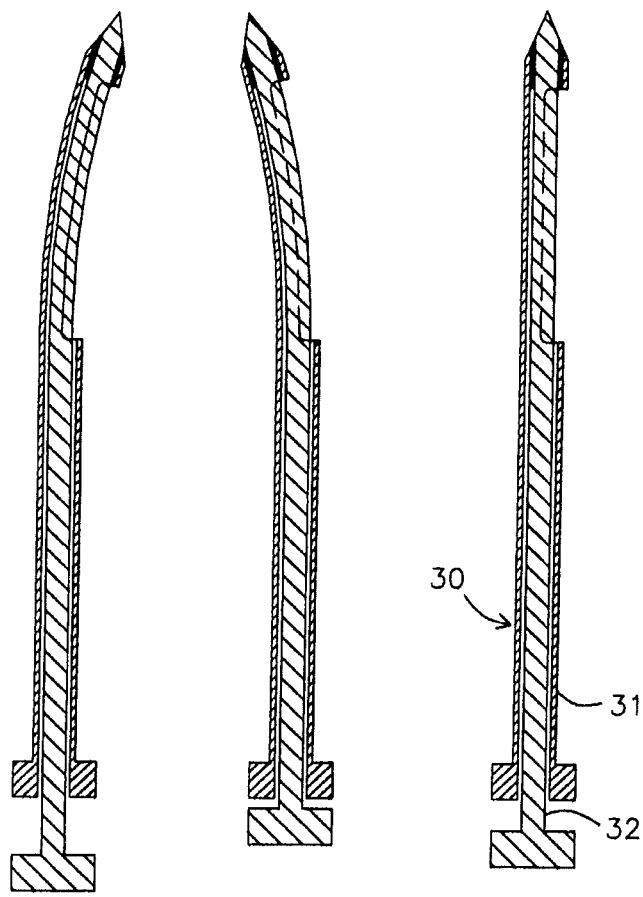

In the embodiments described hitherto, the stationary part has also been the tissue penetrating part, i.e. a stationary part constitutes the most distal portion of a mandrel according to the present invention. In another embodiment, which is illustrated in FIG. 5a to FIG. 5e, a mandrel 30 is illustrated. The mandrel 30 comprises a stationary part 31 and a movable part 32. The stationary part 31 is basically an elongated tubular sleeve 31, in a distal portion of which a semi-circular piece has been cut away, such that the sleeve 31 is provided with an opening, e.g. a notch, gap or recess 33, which—in comparison with the notch or gap 6 of the embodiment described in conjunction with FIGS. 1 and 2—is rather long. The recess 33 does, however, not extend all the way to the distal end of the tubular sleeve 31, but ends a short distance proximally of the distal end of the tubular sleeve 31, such that the stationary part 31 comprises a rather short end portion 34 having a circular cross-section, as can be seen, e.g., in the distal cross-section of FIG. 5a. The movable part 32 is basically an elongated rod-like member 32 having a proximal handle 35. The movable part 32 is slidable within the proximal portion of the tubular stationary part 31 (as can be seen, e.g., in the proximal cross-section of FIG. 5a), but at a distal portion thereof the movable part 32 is attached inside the circular end portion 34 of the stationary part 31. Glue or solder can, for example, be used to attach a distal portion of the movable part 32 to the circular end portion 34 of the stationary part 31. In the distal cross-section shown in FIG. 5a, an attachment layer has been indicated by the reference numeral 36. The distal portion of the movable part 32 continues, however, beyond the end portion 34 of the stationary part 31 to end in a distal end 37, which, for example, can be sharp or blunt. In this embodiment, the movable part 32 thereby constitutes the most distal portion of the steerable mandrel 30. It is, however, possible that a movable part ends within a short end portion of a stationary part, which is provided with a blunt or sharp distal end, which then constitutes the distal end of a mandrel. Further, by choosing the length of the end portion 34, the bending and thereby the steering properties of the mandrel 30 can be influenced. With a short end portion 34, the mandrel 30 bends smoothly from its very distal end (see, e.g., FIGS. 5d and 5e), whereas a longer end portion 34 provides a mandrel 30 that bends at a more proximal location and has a more or less straight distal end portion The functioning of the mandrel 30 is illustrated in FIGS. 5c to 5e. More specifically, FIG. 5c shows the mandrel 30 in a first or neutral position, wherein there is essentially no force acting between the stationary part 31 and the movable part 32. In FIG. 5d, the movable part has been pushed into the stationary part, and—since the movable part is attached to the distal end of the stationary part—this movement causes a bending of the mandrel 30. A bending in the opposite direction is accomplished by retracting the movable part out of the stationary part, as is illustrated in FIG. 5e.

Further, the mandrel 30 can—like mandrel 1 described above—be used together with another, separate sleeve, to thereby form a steerable medical penetration instrument.

This application is based on U.S. Provisional Applications 61,147,844, filed Jan. 28, 2009, and 61/187,057, filed Jun. 15, 2009, both of whose entire contents are incorporated herein by reference.

In some embodiments, the mandrel is 1 mm, 2 mm, 3 mm, 4 mm, 5 mm, 6 mm, 7 mm, 8 mm, 9 mm, or 10 mm in diameter and 10 cm, 20 cm, 30 cm, or 40 cm long. The invention also includes methods of using the described devices.

Although the present invention has been described with reference to specific embodiments, also shown in the appended drawings, it will be apparent to those skilled in the art that many variations and modifications can be done within the scope of the invention as described in the specification and defined with reference to the claims below. It is, for example, within the scope of the present invention that an opening in a stationary part instead is a weakened section of a mantle wall of stationary part, i.e. that the weakened section has an elasticity which is high in comparison with the circumferentially opposite side of the weakened section, or that an opening in the mantle wall of a stationary part is covered with an elastic material, such as plastic, rubber or silicone. Preferably, the mandrel can thereby be provided with a smooth outer surface.

The invention claimed is:
1. A steerable medical instrument comprising:
   a sleeve; and
   a mandrel, wherein the mandrel is adapted to be introduced into and slidable within the sleeve, the mandrel including:
      a stationary part, the stationary part comprising a tubular sleeve having a mantle wall with a longitu- dinal semi-circumferential opening or weakening, which divides the stationary part into a proximal portion on the proximal side of the opening or weakening and a distal portion on the distal side of the opening or weakening, a movable part comprising a rod-like member, the rod-like member being slidable within the proximal portion of the stationary part, wherein the movable part is attached to the distal portion of the stationary part, wherein the stationary part further comprises an end portion at the distal portion, the end portion having a circular cross-section, and wherein a distal portion of the movable part is attached to the end portion of the stationary part, the movable part ending in a distal end portion which extends beyond the distal end portion of the stationary part, to thereby form a distal end of the mandrel, wherein the distal end portion of the moveable part of the mandrel is sharp, and wherein the movable part, at its proximal end, is provided with an elongated pivotable handle with a first end and a second end and with a pivot point located at a first end of the elongated pivotable handle, said pivot point being at a junction between the elongated handle and an elongated piston-like member and causing the handle to radiate outwardly from the elongated piston-like member, wherein a neutral position of the elongated pivotable handle is defined as a position where the longitudinal extension of the handle is directed along a longitudinal axis of the mandrel, and when said handle is in its neutral position the mandrel is essentially straight/unbent, and wherein the pivotable handle is pivotable in a first direction in relation to the longitudinal axis of the mandrel such that the distal portion of the stationary part is bent in the same direction as the handle in relation to the longitudinal axis of the mandrel and the mandrel further comprising at the proximal end an expanded portion having a knurled area wherein rotating the expanded, knurled area provides rotation of the mandrel in relation to the sleeve.

2. The steerable medical instrument according to claim 1, wherein the handle is pivotable in a second direction such that the distal portion of the stationary part is bent in a second bending direction, opposite to the first bending direction.

3. The steerable medical instrument according to claim 2, wherein the first bending direction corresponds to the first pivot direction such that the first pivot direction of the handle is indicative of the first bending direction of the distal portion of the stationary part and wherein the second bending direction corresponds to the second pivot direction such that the second pivot direction of the handle is indicative of the second bending direction of the distal portion of the stationary part.

4. The device of claim 1, wherein said mandrel is removable from said sleeve.

* * * * *